United States Patent [19]

Angstadt

[11] Patent Number: 4,888,231

[45] Date of Patent: Dec. 19, 1989

[54] ABSORBENT CORE HAVING A DUSTING LAYER

[75] Inventor: John J. Angstadt, Cincinnati, Ohio

[73] Assignee: The Procter & Gamble Company, Cincinnati, Ohio

[21] Appl. No.: 68,598

[22] Filed: Jun. 30, 1987

Related U.S. Application Data

[63] Continuation of Ser. No. 868,217, May 28, 1986, abandoned.

[51] Int. Cl.$^4$ .............. A61F 13/16; B32B 5/16; B32B 5/26; B32B 5/30
[52] U.S. Cl. .................... 428/213; 19/148; 19/302; 428/74; 428/76; 428/283; 428/286; 428/287; 428/298; 428/303; 428/311.1; 428/311.5; 428/311.7; 428/311.9; 428/319.7; 428/319.9; 428/339; 428/913; 604/368; 604/370; 604/372; 604/375; 604/376; 604/378; 604/385.1
[58] Field of Search .............. 428/213, 283, 286, 287, 428/339, 913; 604/368

[56] References Cited

U.S. PATENT DOCUMENTS

| | | |
|---|---|---|
| 3,670,731 | 6/1972 | Harmon . |
| 4,102,340 | 7/1978 | Mesek et al. . |
| 4,297,410 | 10/1981 | Tsuchiya et al. .................... 428/283 |
| 4,333,463 | 6/1982 | Holtman . |
| 4,340,556 | 7/1982 | Ciencewicki ...................... 264/119 |
| 4,364,992 | 12/1982 | Ito et al. . |
| 4,537,590 | 8/1985 | Pieniak et al. ...................... 604/379 |
| 4,604,313 | 8/1986 | McFarland et al. ................ 428/172 |
| 4,610,678 | 9/1986 | Weisman et al. ................... 604/368 |
| 4,650,479 | 3/1987 | Insley ................................ 604/358 |
| 4,655,757 | 4/1987 | McFarland et al. ................ 604/366 |
| 4,673,402 | 6/1987 | Weisman et al. .................... 604/368 |

*Primary Examiner*—James C. Cannon
*Attorney, Agent, or Firm*—Steven W. Miller; John M. Pollaro; Fredrick H. Braun

[57] ABSTRACT

Airlaid fibrous webs having a primary layer having discrete particles of absorbent gelling material dispersed through at least a portion of the web airlaid over a dusting layer of essentially hydrophilic fiber material. The dusting layer acts to block the passage of particles injected in the stream of fibers forming the primary layer so as to minimize equipment plugging problems and the loss of particles or fibers through the foraminous forming element and to provide a more efficient absorbent core.

10 Claims, 7 Drawing Sheets

ABSORBENT CORE HAVING A DUSTING LAYER

This application is a continuation of application Ser. No. 06/868,217 filed on May 28, 1986, and now abandoned.

FIELD OF THE INVENTION

This invention relates to airlaid fibrous webs having discrete particles dispersed through at least a portion of the web. More particularly, it relates to an absorbent core for use in an absorbent article that has a dusting layer of fibers formed by depositing a layer onto the foraminous forming element of an airlaying apparatus prior to depositing a layer of fibers mixed with discrete particles of a material such as an absorbent gelling material on the foraminous forming element so as to minimize the loss of such particles through the foraminous forming element and to provide an effective absorbent core.

BACKGROUND OF THE INVENTION

Absorbent gelling materials (AGM's) are polymeric materials which are capable of absorbing large quantities of fluids such as body fluids and wastes and which are further capable of retaining such absorbed fluids under moderate pressures. These absorption characteristics of absorbent gelling materials make such materials especially useful for incorporation into absorbent articles such as disposable diapers, incontinent pads and catamenial napkins. For example, Procter & Gamble; European patent application EP-A-122,042; published Oct. 17, 1984 discloses absorbent structures wherein discrete particles of absorbent gelling material (hydrogel particles) are dispersed in a web of hydrophilic fibers. Additionally, U.S. patent application Ser. No. 734,426 filed on May 15, 1985, now U.S. Pat. No. 4,673,402 issued June 16, 1987, by Paul T. Weisman, Dawn l. Houghton and Dale A. Gellert discloses an absorbent article having a dual-layer absorbent core wherein a shaped core component consists essentially of hydrophilic fiber material and an insert core component consists essentially of a substantially uniform combination of hydrophilic fiber material and discrete particles of absorbent gelling material.

However, several difficulties have been encountered in airlaying absorbent cores having a multiplicity of layers and/or layers containing a mixture of fibers and particular amounts of discrete particles of materials such as absorbent gelling materials. Airlaying apparatus and methods require the removal of the gas or air which transports the fiber/particle admixture from beneath the foraminous forming element of the airlaying apparatus. During this removal, small particles which are mixed with the fibers can generally be drawn along with the air through the voids in the foraminous forming element, resulting in a loss of expensive absorbent gelling materials through the airlaying apparatus, the resultant absorbent article also having a reduced quantity of absorbent gelling material dispersed throughout its absorbent core resulting in a loss of absorbent capacity in the articles. Additionally, relatively large particles tend to plug or block the flow of air through the foraminous forming element resulting in a loss of uniformity of basis weight across or along the fibrous web or absorbent core as well as machinery down time necessitated in order to unplug the foraminous forming element. Thus, it would be advantageous to provide an airlaid fibrous web having discrete particles of material, such as absorbent gelling materials, dispersed through at least a portion of the web without having reduced design quantities of materials in the core and with uniform basis weights across or along the material-containing layer of the web.

Accordingly, it is an object of the present invention to provide airlaid fibrous webs having discrete particles dispersed through at least a portion of the web.

It is a further object of the present invention to provide an absorbent core wherein fibers or fiber/particle admixtures are airlaid over a dusting layer to minimize loss of particles, to provide more uniform and efficient cores, and to provide more efficient and effective use of absorbent gelling materials.

SUMMARY OF THE INVENTION

It a particularly preferred embodiment, the present invention comprises airlaid fibrous webs having a primary layer of discrete particles of absorbent gelling material dispersed through at least a portion of the web that is airlaid over a dusting layer of essentially hydrophilic fibers. The dusting layer acts to block the passage of particles or fibers entrained in the primary layer so as to minimize equipment plugging problems and the loss of particles or fibers through the foraminous forming element. In addition, the dusting layer acts as a wicking layer, preferably adjacent the backsheet, to provide improved liquid acquisition and distribution by quickly acquiring liquids that migrate, such as by gravity, to the backsheet-side of the core and by transporting such liquids to the primary layer for storage of such liquids.

The present invention also relates to dual-layer cores and absorbent articles utilizing such absorbent cores having a dusting layer overlaid by a primary layer.

BRIEF DESCRIPTION OF THE DRAWINGS

While the specification concludes with claims particularly pointing out and distinctly claiming the present invention, it is believed the present invention will be better understood from the following description in conjunction with the accompanying drawings in which:

DETAILED DESCRIPTION OF THE INVENTION

While the present invention will be described in detail in the context of providing airlaid fibrous webs for use as absorbent cores in absorbent articles such as disposable diapers, the present invention is in no way limited to such an application. The present invention may be employed with equal facility to provide airlaid fibrous webs for later incorporation into a number of articles, including incontinent briefs, sanitary napkins, bandages and the like.

Figure 10:
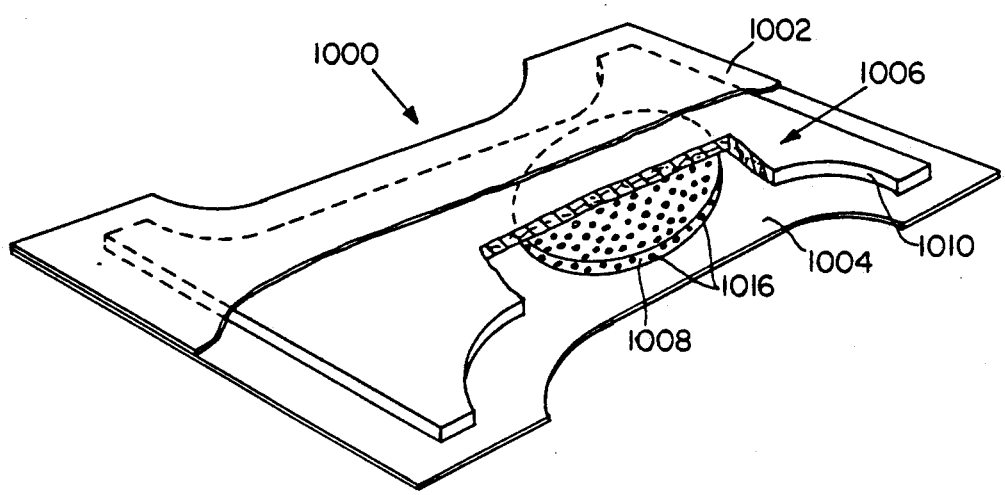
FIG. 10 is a cut-away view of a preferred disposable absorbent article such as a diaper having a dual-layer absorbent core formed by the apparatus and methods of the present invention.

FIG. 10 shows a particularly preferred embodiment of a disposable diaper having an absorbent core of the present invention. The disposable diaper 1000 comprises a topsheet 1002, a liquid impervious backsheet 1004, and an absorbent core 1006 disposed between the topsheet 1002 and the backsheet 1004. A preferred construction of such a disposable diaper is described in U.S. Pat. No. 3,860,003, issued Jan. 14, 1975 to Kenneth B. Buell, which patent is herein incorporated by reference.

The absorbent core 1006 preferably comprises two or more distinct core components. The absorbent core comprises an insert core component 1008 (first web component) and a shaped core component 1010 (second web component). This preferred absorbent core is described in more detail in U.S. patent application Ser. No. 734,426, filed May 15, 1985, now U.S. Pat. No. 4,673,402 entitled "Absorbent Articles with Dual-Layered Cores" issued June 16, 1987 to Paul T. Weisman, Dawn l. Houghton, and Dale A. Gellert, which is herein incorporated by reference.

The shaped core component 1010 serves to quickly collect and temporarily hold and distribute discharge body fluid. Thus, the wicking properties of the materials or fibers in the shaped core component 1010 are of primary importance. Therefore, the shaped core component 1010 consists essentially of an hourglass shaped web of hydrophyllic fiber material. While many types of fibers are suitable for use in the shaped core component 1010, preferred types of fibers are cellulose fibers, in particular, wood pulp fibers. While the shaped core component 1010 is preferably free of particles of an absorbent gelling material, the shaped core component 1010 may alternatively contain small amounts of particles of an absorbent gelling material so as to enhance its fluid acquisition properties. Other materials in combination with the fibers may also be incorporated into the core component such as synthetic fibers.

Figure 11:
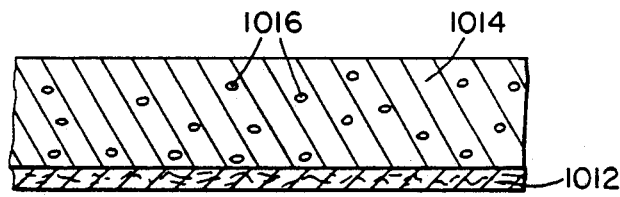
FIG. 11 is an enlarged cross-sectional view of the insert core component of the absorbent core of the diaper shown in FIG. 10.

The insert core component 1008 absorbs discharge body fluids from the shaped core component 1010 and retains such fluids. As shown in FIGS. 10 and 11, the insert core component 1008 consists essentially of a thin dusting layer 1012 of hydrophyllic fiber material overlayed by a primary layer 1014 of a uniform combination of hydrophyllic fiber material and particular amounts of discrete particles 1016 of substantially water-insoluble, fluid absorbing, absorbent gelling materials. The hydrophyllic fibers in the insert core component 1008 are preferably of the same type as those herein described for use in the shaped core component 1010. There are several suitable absorbent gelling materials which can be used in the insert core component, such as silica gels or organic compounds such as crosslinked polymers. Particularly preferred absorbent gelling materials are hydrolyzed acrylonitrile grafted starch, acrylic acid grafted starch, polyacrylates and isobutylene maleic anhydride copolymers, or mixtures thereof.

While the dusting layer 1012 of the absorbent core 1006 is preferably a relatively thin layer of hydrophillic fiber materials, it should be understood that the term "dusting layer", used herein to denote a certain layer of the fibrous web or as a prefix to identify certain elements which form or are used to form the dusting layer, should not be limited to such a thin layer, but includes embodiments wherein such a layer may be any thickness. For example, the dusting layer is preferably about 1.0 inch to about 1.5 inch (about 25 mm to about 38 mm) thick with about 1.25 inches (about 31.75 mm) being especially preferred, although thicker or thinner layers are contemplated.

Figure 1:
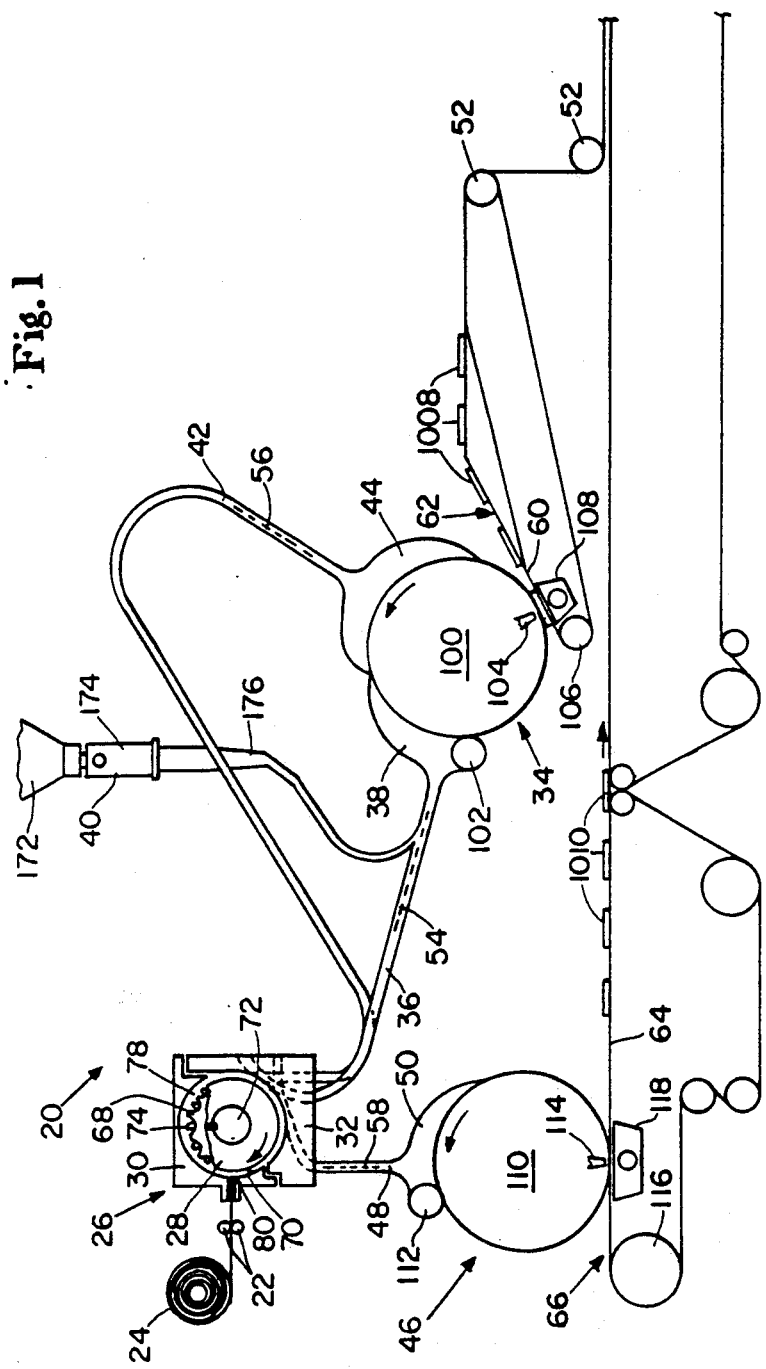
FIG. 1 is a partially cut-away side view of a preferred apparatus of the present invention.

FIG. 1 discloses a particularly preferred embodiment of the apparatus for forming airlaid fibrous webs having a multiplicity of components such as the absorbent core 1006 of the disposable diaper 1000 that is shown in FIGS. 10 and 11. In the embodiment illustrated in FIG. 1, the apparatus 20 is shown to comprise a pair of counter-rotating metering infeed rolls 22 for directing a roll 24 of drylap material into engagement with a disintegrator 26, the disintegrator 26 having a rotary disintegrating element 28 partially enclosed by a housing 30; a splitting means or apparatus such as a splitter chute 32 for providing a multiplicity of streams of air-entrained fibers; a first airlaying means such as a drum-type airlaying apparatus 34 for forming a first web component; a first deposition means such as a first deposition chute 36 and hood 38 for directing a first stream of air-entrained fibers to the first airlaying means and for depositing the fibers on the first airlaying means; an absorbent gelling material injection apparatus 40 or means for mixing discrete particles of an absorbent gelling material with the stream of air-entrained fibers that is directed through the first deposition chute 36; a dusting layer deposition means such as a dusting layer deposition chute 42 and hood 44 for directing a dusting layer stream of air-entrained fibers to the first airlaying means and depositing the fibers on the first airlaying means; a second airlaying means such as a second drum-type airlaying apparatus 46 for forming a second web component; a second deposition means such as a second deposition chute 48 and hood 50 for directing a second stream of air-entrained fibers to the second airlaying means and for depositing the fibers onto the second airlaying means; and a uniting means such as a uniting roll apparatus 52 for uniting the first and second web components. In order to simplify the disclosure, several elements or means which can readily be supplied by those skilled in the art have been omitted from the drawings. Such elements include structural members, bearings, power transmission units, controlling units and the like. Additionally, a first stream 54 of air-entrained fibers is shown in FIG. 1 to be moving through the first deposition chute 36; a dusting layer stream 56 of air-entrained fibers is shown to be moving 32 through the dusting layer deposition chute 42; a second stream 58 of air-entrained fibers is shown to be moving through the second deposition chute 48; an endless stream of insert core components 1008 (first web components) is shown moving on the belt 60 of a first take-away conveyor 62; and an endless stream of shaped core components 1010 (second web components) is shown moving on the belt 64 of a second take-away conveyor 66.

A preferred embodiment of a disintegrator 26 is shown in FIG. 1 to comprise a rotary disintegrating element 28 partially enclosed in a housing 30. A similar-type disintegrator is shown in U.S. Pat. No. 3,863,296, issued on Feb. 4, 1975 to Kenneth B. Buell, which patent is herein incorporated by reference. However, as used herein, the term "disintegrator" s not intended to limit the present invention to apparatus of the type illustrated in the above patent, but includes apparatus such as hammermills, fiberizers, picker rolls, lickerin rolls or any other apparatus which separates a roll or mat of fibrous material into its individual fibers.

As used herein, a fibrous or drylap material or sheet describes any type of fibrous sheet material capable of disintegration into individual fibers. For example, the fibrous material can include fibers of rayon, polyester, cotton or the like, with cellulosic fibers being especially preferred.

The disintegrator 26 preferably comprises a rotary disintegrating element 28 comprising a plurality of rotors 68 and a housing 30 having a generally cylindrical bore 70. A shaft 72 is journaled in the closed ends of the housing 30 such that one end of the shaft 72 extends outside the housing 30 to permit coupling the shaft in a conventional manner to a motive power source such as an electric motor (not shown). The motor continuously drives the shaft 72 in the direction as shown. The rotors 68 are keyed to the shaft 72 in juxtaposed relation, each being provided with a plurality of teeth 74 extending outwardly such that their tips are adapted to serve as impacting elements. As used herein, "rotor" refers to thin rotored discs. With the above arrangement, successive teeth 74 impact the end of the infeeding sheet 24 as the rotors are turned. The rotors 68, when keyed into place and molded together, form an axial rotary cylindrical disintegrating element 28 rotatable about its cylindrical axis. This configuration is preferred since it permits the favorable internal distribution of stresses set up during operation of the disintegrator 26.

The housing 30 partially encloses the disintegrating element 28 and defines a flow channel 78 for a column of fibers between the disintegrating element and the housing. The flow channel 78 is sized to give from about one thirty-second to about one-fourth inch (about 0.79 mm to about 6.35 mm) clearance between the blade tips of the disintegrating element 28 and the housing 30 so as to direct the column of fibers from the inner end of the housing toward the splitter chute 32. The housing 30 has a cylindrical bore 70 to partially enclose the disintegrating element 28 and an inlet portion 80 which is slotted to provide an inlet opening having an inner end. (While the housing 30 may alternatively be comprised of additional elements, such are not preferred in the present invention). The inlet opening 80 is disposed so as to receive the fibrous sheet 24 and guide it to the inner end, which defines a sheet support element, whereat an edge of the fibrous sheet 24 is disintegrated.

With the above arrangement, successive teeth 74 impact the end of the infeeding drylap sheet 24 as the rotors 68 are turned to separate the fibers of the fibrous sheet 24 into individual fibers. After separation of the fibers of the fibrous sheet into the individual fibers, a column of fibers is formed across the axial width of the housing 30. As used herein, "a column of fibers" denotes a pattern or system of fibers disposed across the axial width of the housing. The rotation of the disintegrating element 28 imparts an inherent velocity to the fibers across the axial width of the housing 30, whereupon a continuous column of fibers is directed around the flow channel 78 toward the splitter chute 32.

As shown in FIG. 1, the splitter chute 32 is preferably joined to the housing 30 of the disintegrator 26. The term "joined" includes embodiments wherein the splitter chute 32 is a separate element directly or indirectly connected to or within the housing 30 (i.e. integral) or embodiments wherein the splitter chute 32 is the same element as the housing 30 so that the splitter chute 32 is a continuous and undivided element of the housing 30 (i.e. unitary). While the splitter chute 32 may be an independent apparatus from the disintegrator 26, or the splitter chute 32 may be unitary with the housing 30 of the disintegrator 26, such embodiments are not preferred. The splitter chute 32 is preferably an integral member that is joined into the housing 30 of the disintegrator 26.

Figure 2:
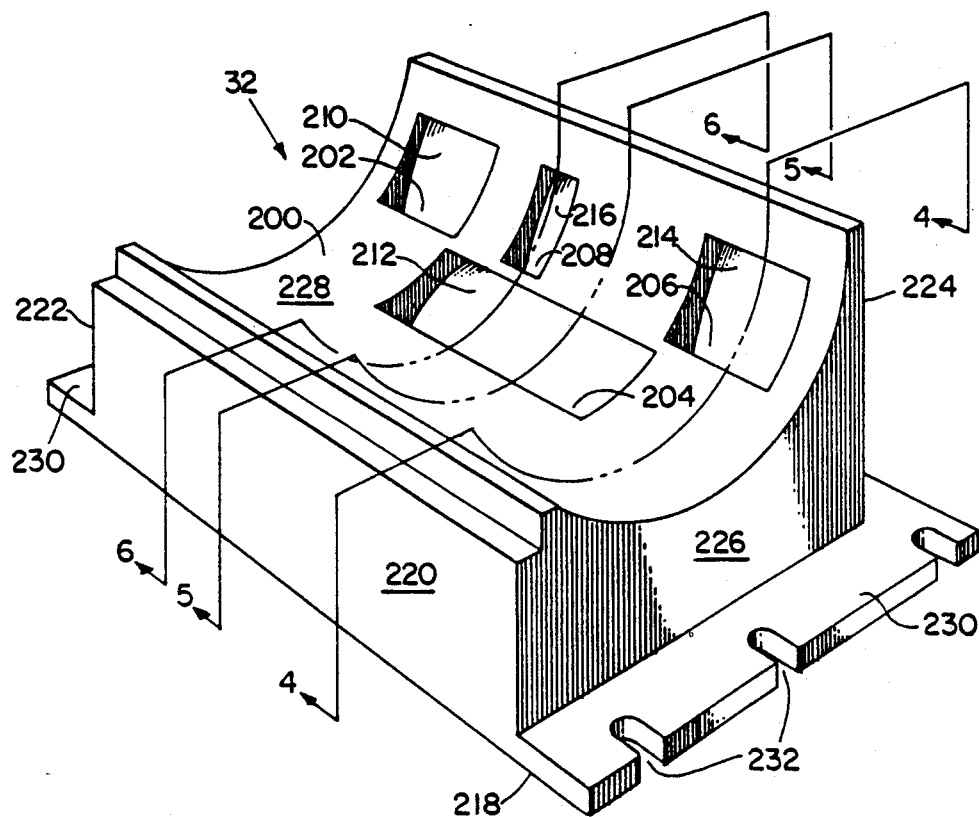
FIG. 2 is a perspective view of the splitter chute apparatus of the present invention.

FIG. 2 shows a particularly preferred embodiment of an apparatus (splitting means or splitter chute 32) for forming a multiplicity of streams of air-entrained fibers by splitting a column of fibers into a multiplicity of fiber streams and independently entraining each of the fiber streams in air. As shown in FIG. 2, the apparatus comprises a splitting member 200 having a number of ports disposed in and along its surface. As shown, the ports are designated a first port 202, a second port 204, a third port 206, and a dusting layer port 208. The apparatus also comprises multiple independent conduit means, such as conduit ducts, for directing high velocity columns of air past the ports disposed along the stripping member 200. The conduit ducts are designated in FIG. 2 according to which port with which the conduit duct is in communication, so as to define a first conduit duct 210, a second conduit duct 212, a third conduit duct 214 and a dusting layer conduit duct 216.

Figure 3:
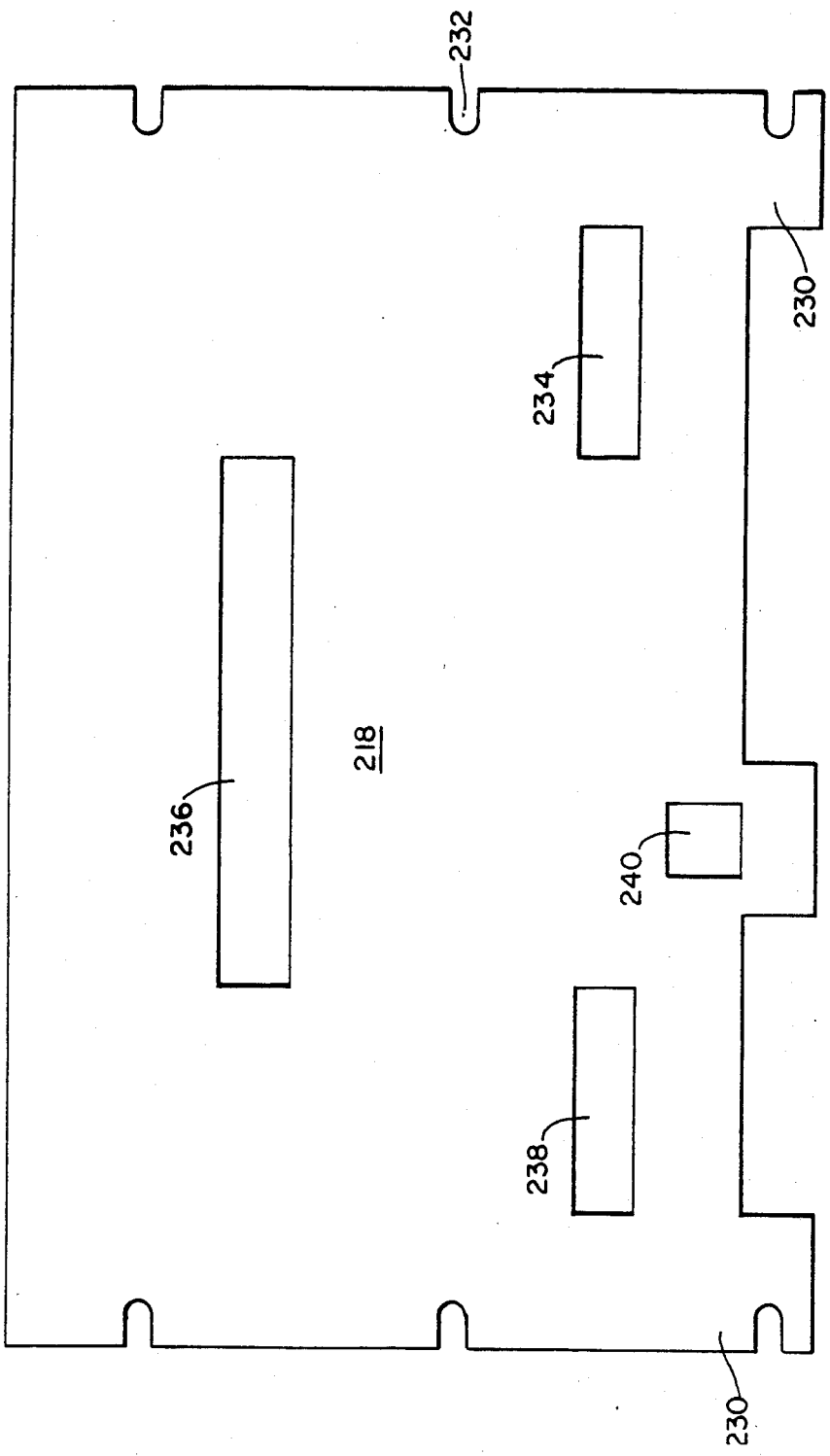
FIG. 3 is a bottom view of the splitter chute apparatus of the present invention.

The splitter chute 32 shown in FIG. 2 is a preferred embodiment of the apparatus of the present invention. The splitter chute is shown in FIG. 2 to additionally comprise a base 218, four side walls 220, 222, 224 and 226, respectively, and a top wall 228 which defines the splitting member 200. The base 218 preferably extends beyond the lateral side walls 222 and 226 to define flanges 230 having bores 232 so that the splitter chute 32 may be bolted or otherwise secured in any conventional manner to the housing 30 of the disintegrator 26. FIG. 3 shows a preferred embodiment of the base 218, the base 218 being shown to accommodate the discharge outlets of each of the conduit ducts. As shown in FIG. 3, the discharge outlets are designated a first discharge outlet 234, a second discharge outlet 236, a third discharge outlet 238 and a dusting layer discharge outlet 240.

The splitting member 200 provides a means for splitting the column of fibers into multiple fiber streams. The splitting member 200 directs the column of fibers to the ports where portions of the column of fibers are split-off into individual fiber streams. The term "splitting member" is used herein to describe a number of different structures having varying configurations and shapes such as ducts, pipes, sheets or combinations of sheets of material, a number of plates in combination, or a number of different elements in combination. The splitting member 200 is shown in FIG. 2 as a curvilinear surface defined by the top wall 228 of the splitter chute 32. However, alternative preferred slitting members include a duct having ports disposed therein or, for example, if the splitter chute 32 is unitary with the housing 30 of the disintegrator 26, the splitting member 200 may comprise a combination of a portion of the disintegrating element 28, the housing 30, and the surface of the top wall 228 of the splitter chute 32, together defining a flow channel 78 through which the column of fibers may be directed.

While the splitting member 200 may have a number of configurations, the surface in which the ports are located or disposed preferably has a curvilinear profile. A curvilinear profile provides angular displacement and velocity components to the fibers to assist in separating and in drawing off the fibers into the individual conduit ducts without the presence of fiber catching mechanical edges or walls such that fiber clumping is minimized. While flat or rectilinear splitting members are contemplated by the present invention, they do not provide this angular displacement advantage as will be described later. In addition, when the splitter chute 32 is joined to the housing 30, a curvilinear splitting member accommodates the shape of the disintegrating element 28. While the curvilinear profile of the splitting member is preferably circular in nature, a number of different curvilinear profiles would be equally preferred such as hyperbolic, parabolic or ellipsoid profiles.

The splitting member 200 may be positioned anywhere relative to where the column of fibers are discharged by the disintegrating element 28. For example, the splitting member 200 of the splitter chute 32 may be positioned relatively for downstream from the disintegrator 26. However, this configuration is not preferred because the column of fibers tends to lose its momentum and is subject to width biasing into fiber wads the farther from the disintegrating element 28 the splitting member 200 is positioned. Thus it has been found that in order to have as clean and accurate a split as possible (a split which provides consistent basis weight fiber streams and minimizes fiber clumping), the splitting member 200 should be positioned as closely as possible to the disintegrating element 28, preferably adjacent to it so that the column of fibers is drawn away from and off of the disintegrating element as it is split into the fiber streams.

As shown in FIG. 2, the splitting member 200 is provided with a number of ports. The ports put the columns of air that are directed through the conduit ducts in communication with the portion of the column of fibers that is directed along the splitting member 200 so that portions of the fiber column may be split-off and drawn into the conduit duct to form a distinct fiber stream. Thus the ports provide an opening for the intake of a stream of fibers into the conduit ducts. While the ports may take a number of shapes and configurations, a preferred configuration of each of the ports is a rectangular-shaped opening having an upstream edge and a downstream or doctor's edge. (These edges are shown and described more particularly in FIGS. 4, 5 and 6).

In order to effectively and efficiently split-off the fibers, at least two ports must be at least partially laterally spaced from each other. As used herein, the term "laterally spaced" is used to denote that a portion of a port is offset to one side of and out of alignment with at least a portion of another port such that a line that is perpendicular to the lateral dimension would not intersect both of the ports. (Lateral being defined as the dimension across the width of the splitting member.) Thus, a partially laterally spaced port denotes that a portion of the first port is disposed to one side of and out of alignment with a potion of the second port. The ports may alternatively and preferably be completely axially offset. In addition, each of the ports may be either longitudinally aligned or spaced downstream or upstream from each other. The term "longitudinally spaced" being used herein to denote that a port is disposed upstream or downstream from another. (Longitudinal being defined as the dimension along the length of the splitting member.) A preferred configuration provides that each successive port be laterally spaced and longitudinally spaced from each successive port. This configuration providing the most efficient split of the fiber column.

As shown in FIG. 2, the first port 202 preferably is disposed adjacent a lateral side wall 222 of the splitter chute 32, an outermost portion of the column of fibers thereby being split-off by the first port 202. The second port 204 is preferably longitudinally spaced downstream and laterally spaced from the first port 202 so as to split-off a second or central width of the column of fibers. The third port 206 is preferably longitudinally aligned with the first port 202 but is laterally spaced from both the first and second ports so as to strip off a third width of fibers from the column of fibers. The dusting layer port 208 which is provided to create a stream of fibers that is used to form the dusting layer, is longitudinally aligned with but laterally spaced from both the first and third ports 202 and 206, but is laterally aligned with but longitudinally spaced from a portion of the second port 204. While the ports may be longitudinally and laterally arranged in a number of different configurations, the configuration shown in FIG. 2 is especially preferred to provide a fibrous web having two core components, one of the components having discrete particles of absorbent gelling material dispersed through one of its layers.

The first and third ports 202 and 206 are preferably centered relative to the second port 204 on the outer edges of the splitting member 200 so as to accommodate variations in the width of the drylap sheet that is fed into the disintegrator 26. Because the fiber streams that are formed from the first and third ports 202 and 206 are merged in the first deposition chute 36 downstream of the splitter chute 32, if there are any major variations in the width of the drylap sheet 24, this variation will not cause a significant change in the basis weight of the web component (insert layer) formed by the first and third fiber streams because they are merged into a combined or primary fiber stream. Thus, the first and third ports 202 and 206 should have equal widths and be positioned symmetrically about the centerline of the splitter chute 32 or splitting member 200.

While the dusting layer port 208 is preferably laterally spaced and longitudinally spaced from all of the ports so that the column of fibers is more efficiently split into four fiber streams, space and size constraints require that the preferred embodiment of the splitter chute 32 have the dusting layer port 208 laterally aligned with a portion of the second port 204 and longitudinally aligned with the first and third ports 202 and 206. The dusting layer port 208 is laterally aligned with a portion of the second port 204 because the second port 204 is preferably much wider than the first and third ports 202 and 206 such that the loss of such a small stream of fibers will have a minimal effect on the ultimate basis weight of the core component formed by the second fiber stream. As shown in FIG. 2, the dusting layer port 208 is preferably laterally spaced from the centerline of the splitter chute 32 toward an edge of the second port 204 so that any effect that the removal of the dusting layer fiber stream has on the basis weight of the hourglass shaped core component is centered along the ears of the shaped core component rather than in the primary absorbent area of the shaped core component.

Figure 4:
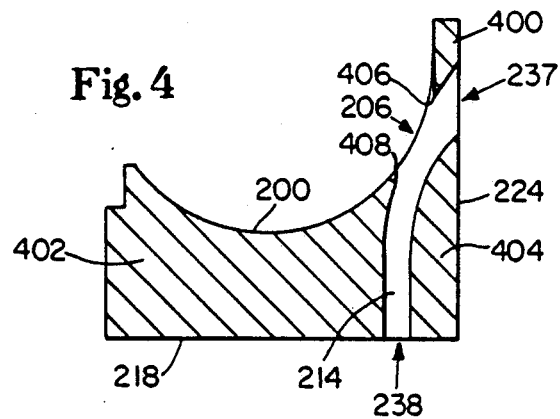
FIG. 4 is a cross-sectional view taken along section line 4—4 of FIG. 2.
Figure 5:
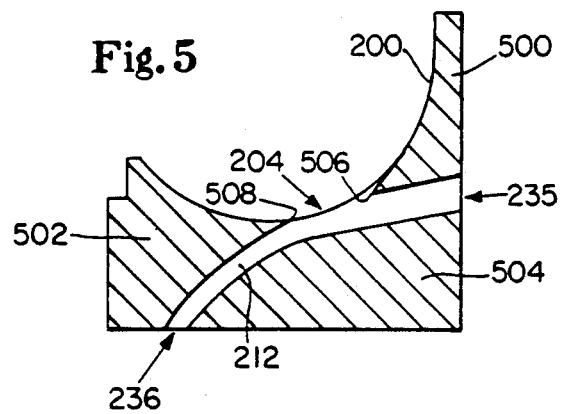
FIG. 5 is a cross-sectional view taken along section line 5—5 of FIG. 2.
Figure 6:
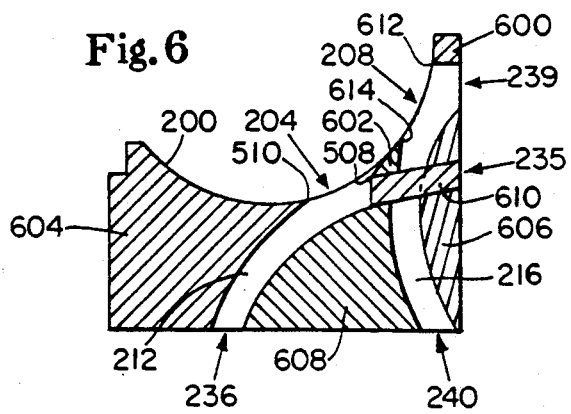
FIG. 6 is a cross-sectional view taken along section line 6—6 of FIG. 2.

The conduit ducts provide a means through which a column of high velocity air as well as streams of air-entrained fibers are directed or conveyed. The conduit ducts may be separated elements such as pipes, channels or ducts which are secured to the splitting member 200 adjacent the ports, or an integral element formed by the positioning of plates as is shown in FIGS. 4, 5 and 6. The conduit ducts should be configured for flow rates of preferably greater than or equal to about 75 ACFM per inch of disintegrating element 28 width and for velocities of preferably greater than or equal to about 6,000 feet per minute, more preferably about 10,000 fpm. Thus it is preferably to make the conduit ducts about 1 inch thick and as wide as required to be in complete communication with the full width of the particular port with which the duct is in communication. While the conduit ducts may have any particular cross-sectional shape, rectilinear ducts or curvilinear ducts having a radius of curvature greater than about 6 inches are especially preferred. While rectilinear conduit chutes minimize air and fiber turbulence within the ducts, especially when such ducts are disposed tangentially to the curvilinear surface of the splitting member 200 adjacent that particular port, curvilinear ducts are especially preferred due to size and shape constraints and equipment arrangement.

The inlets of the conduit ducts provide a means to inject or draw ambient air into the conduit ducts at relatively high velocities. While the inlet ports may take on a number of different configurations, a configuration having an aerodynamic shape is believed to function to minimize air turbulence as the air is drawn into the conduit duct.

A preferred configuration of the discharge outlets along the base 218 of the splitter chute 32 is shown in FIG. 3. The first and third discharge outlets 234 and 238 are preferably aligned across the width of the base so that the first deposition chute 210 which merges the fiber streams downstream may conveniently be secured to both discharge outlets. The dusting layer discharge outlet 240 is slightly offset from the first and third discharge outlets 234 and 238 to more easily accommodate the dusting layer deposition chute. The second discharge outlet 236 is set apart from all of the other discharge outlets due to the configuration of the second conduit duct and to facilitate equipment arrangements of two laydown drums.

The percentage of the total airfelt weight per absorbent core that will form each of the specific core components will vary according to the size of the absorbent article that is being manufactured. Thus a large diaper may require a greater percentage of the total airfelt weight in the shaped core component than a medium diaper. Because the axial width of the ports determine the percentage of airfelt dedicated to each core component, it is preferably that the axial width of each port across the total axial width of the splitting member 200 be able to be changed according to the core component airfelt weights. Accordingly, the splitter chute 32 is preferably manufactured from a series of plates that are bolted or otherwise secured together in any conventional manner to form varying size chambers so that the width of each port, and correspondingly the width of each conduit duct, may be varied to accommodate the particular basis weight required in the final core component.

FIG. 4 shows a cross-sectional view of a preferred embodiment of the splitter chute 32 taken along sectional line 4—4 of FIG. 2. The cross-sectional view illustrates the configuration of the splitting member 200, the third port 206, and the third conduit duct 214 having an inlet 237 and a discharge outlet 238 in the third chamber or splitting region of the splitter chute 32. (While the present invention will be described with reference to the third chamber or splitting region, it should be understood that the description is equally applicable to the first chamber or splitting region.) The above elements are preferably formed and defined by three plates comprising a top plate 400, a downstream plate 402, and a base plate 404.

The top plate 400 defines a portion of the top wall 228 or splitting member 200 of the present invention as well as a top wall of the third conduit duct 214, a portion of the inlet 237, and the upstream edge 406 of the third port 206. The portion of the top plate 400 that defines the upstream edge 406 of the third port 206 is shown to be tapered away from the circular profile of the splitting member 200. This configuration is preferred so that the portion of the column of fibers directed in the third chamber will begin to depart from the disintegrating element 28 due to the lack of constraint provided by the tapered upstream edge 406 as well as the fact that each fiber has an angular velocity component directed tangentially to its angular path which tends to direct or release the fibers away from the disintegrating element 28.

The downstream plate 402 defines the portion of the splitting member 200 that is downstream of the third port 206, a portion of a wall of the third conduit duct 214, and a portion of the base 218 of the splitter chute 32. Additionally, the downstream plate 402 defines the downstream edge or doctor's edge 408 of the third port 206. In conventional disintegrating apparatus, this doctor's edge is a point where a significant amount of the fibers are removed from the teeth of the disintegrating element and directed into a conduit duct. The result of this removal at the doctor's edge causes a significant amount of fiber clumping along the doctor's edge. However, the term "doctor's edge" is used herein for descriptive purposes. Very little, if any, fibers are removed from the teeth 74 of the disintegrating element 28 by this edge. Most of the fibers are removed by the effects of the pressure differential established adjacent the port and the angular velocity and momentum of the fibers as the fibers are drawn or pulled away from the disintegrating element. Thus, there is reduced fiber clumping along this doctor's edge 408.

The base plate 402 defines a wall of the third conduit duct 214, as well as a portion of the base 218 and side wall 224 of the splitter chute 32.

FIG. 5 shows a cross-sectional view of a preferred embodiment of the splitter chute taken along sectional line 5—5 of FIG. 2. The cross-sectional view illustrates the configuration of the splitting member 200, the second port 204, and the second conduit duct 212 having an inlet 235 and a discharge outlet 236 in the second chamber or splitting region of the splitter chute 32. (This portion of the second chamber is where no dusting layer fiber stream is formed.) The above elements are preferably formed and defined by three plates comprising a top plate 500, a downstream plate 502 and a base plate 504. These plates are arranged in a similar manner and define similar portions of the splitter chute as the plates shown in FIG. 4 except that the second port 204 and the second conduit ducts 212 are arranged downstream along the splitting member 200 from where the first and third ports 202 and 206 are disposed. The upstream edge 506 and the doctor's edge 508 of the second port are also shown in FIG. 5.

FIG. 6 shows a cross-sectional view of a preferred embodiment of the splitter chute 32 taken along sectional line 6—6 of FIG. 2. The cross-sectional view illustrates the configuration of the splitting member 200, the dusting layer port 208, the second port 204, the dusting layer conduit duct 216 having an inlet 239 and a discharge outlet 240 and the second conduit duct 212 having an inlet 235 and a discharge outlet 236, in the dusting layer chamber or splitting region of the splitter chute. While the dusting layer chamber may be configured in a number of different ways, including the configuration shown in FIG. 4 wherein the second port and duct would not be formed in the dusting layer chamber, such embodiments are not preferred. The above elements are preferably formed and defined by six plates comprising a top plate 600, an intermediate plate 602, a downstream plate 604, a side plate 606, a base plate 608, and a wedge plate 610.

The splitting member 200 is formed from the top surface of the top plate 600, the intermediate plate 602 and the downstream plate 604. The intermediate plate 602 acts as a separator to define the ports. The dusting layer port 208 is defined by the top plate 600 and the intermediate plate 602; the top plate 600 defining the upstream edge 612 of the dusting layer port 208 and the intermediate plate 602 defining the doctor's edge 614 of the dusting layer port 208. The second port 204 is defined by the intermediate plate 602 and the downstream plate 604; the intermediate plate 604 defining the upstream edge 508, and the downstream plate 604 defining the doctor's edge 510 of the second port 204. The dusting layer conduit duct 216 is formed by the top plate 600, the side plate 606, the intermediate plate 602, and the base plate 608. The second conduit duct 212 is defined by the intermediate plate 602, the downstream plate 604 and the base plate 608. It should be noted that the second conduit duct 212 is blocked by the wedge plate 610. The wedge plate 610 is a plate having tapered ends and a square hole cut vertically through the plate so as to block the flow of air through the portion of the second conduit duct 212 which is in communication with the dusting layer conduit duct 216 while permitting the flow of air through the dusting layer conduit duct 216.

A particularly exemplary splitter chute 32 is configured of twenty-seven sets of plates across its width, each of the plates having a width of about five-eights inch (about 15.8 mm). Thus, the cumulative width of the splitter chute 32 is about seventeen inches (about 432 mm). The first and third chambers are configured of from about four to about eight plates each such that the first and third ports 202 and 206 each have a width of about 2.5 to about 5.0 inches (about 63.5 to about 127 mm). The second chamber is configured of from about thirteen to about twenty plates such that the width of the second port 204 is about 8.12 to about 12.5 inches (about 206 to about 317.5 mm). Of these thirteen to twenty plates, about two to four plates are configured to provide the dusting layer chamber such that the dusting layer port 208 has a width of about 1.25 to about 2.5 inches (about 31.75 to about 63.5 mm.). The dusting layer chamber being laterally spaced from the first chamber by at least two plates or about 1.25 inches (about 31.75 mm).

The splitter chute 32 is preferably operated such that each column of air that is drawn through the conduit ducts has a velocity of about six-thousand to about fifteen-thousand feet per minute (about 1.83 to about 4.57 km per minute), preferably about ten-thousand feet per minute (3.05 km per minute) and a flow rate of from about 40 to about 100 ACFM per inch, preferably about 75 ACFM per inch.

Figure 7:
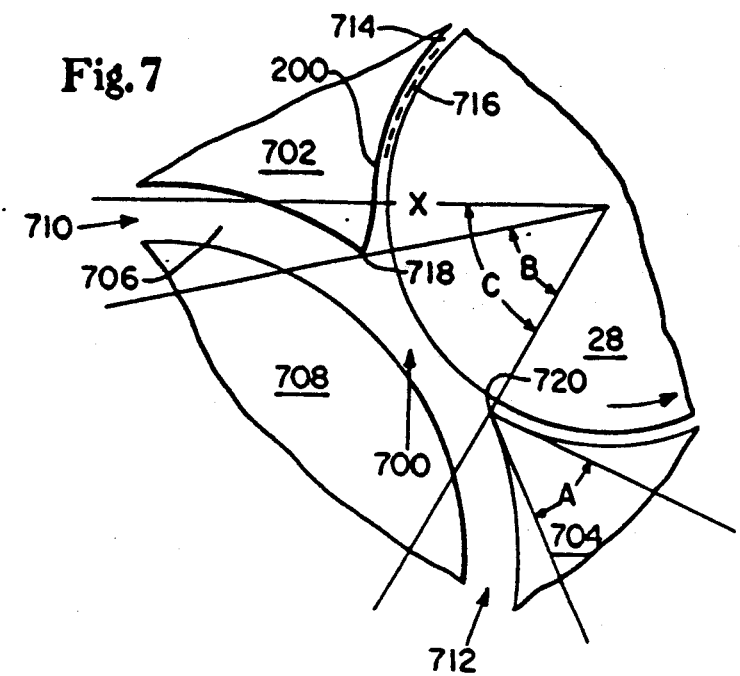
FIG. 7 is an enlarged cross-sectional illustration of a transition zone of a splitter chute apparatus.
Figure 8:
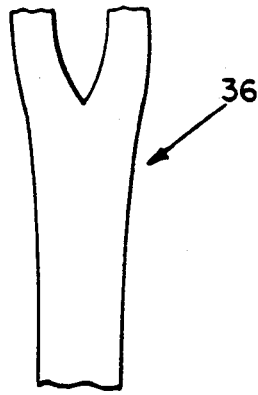
FIG. 8 is a schematic illustration of the first deposition chute of the present invention.

FIG. 7 shows an expanded cross-sectional view of a preferred embodiment of the splitter chute 32 adjacent any of the ports of the present invention. The disintegrating element 28 is shown to be rotating in a computer-clockwise direction. The splitting member 200 having a port 700 is shown to be a curvilinear surface formed by a top plate 702 and a downstream plate 704. The conduit duct 706 is formed from the surfaces of the top plate 702, the downstream plate 704 and the base plate 708, the inlet of the conduit duct 706 being designated 710 and the discharge outlet being designated 712. Also as shown in FIG. 7, the disintegrating element 28, the splitting member 200, and the housing (not shown) define a narrow flow channel 714 through which the column of fibers 716 is directed. The upstream edge 718 of the port 700 (the edge of the top plate 702 adjacent the port 700) is shown in FIG. 7 to be tapered away from the disintegrating element 28. (As previously discussed, this configuration is preferred so that the fibers may begin to release from the disintegrating element.) The doctor's edge 720 or downstream edge of the port 700 (the edge of the downstream plate 704 adjacent the port 700) is shown to have an included angle "A" as defined by the tangents to the surfaces of the plate. A tangent release point, designated by the "X" in FIG. 7, is the point defined wherein the tangential component of angular velocity of the fiber is such that the fiber tends to release from its angular path away from the disintegrating element 28. While the tangent release point may be positioned either upstream or adjacent the port 700, it is preferable that the tangent release point be configured slightly upstream of the port 700 to provide the maximum stripping effect while minimizing clumping.

It has been found that the geometry of the members may have an important determination upon whether fiber clumping can be minimized. The angle "8" formed between the upstream edge 718 and the doctor's edge 720 defines the actual opening of the port 700. The actual opening is preferably not greater than about 60°, more preferably about 15° to about 45° and most preferably about 30°. The angle "C" defined by the angle between the tangent release point, X, and the doctor's edge 720 defines an effective opening of the port 700. The effective opening is preferably not greater than about 75°, more preferably about 30° to about 60°, and most preferably about 40° to about 45°. Thus the tangent release point should not be disposed upstream of the port 700 by more than about fifteen degrees (15°). It has also been found that the included angle, angle "A", is preferably about 15° to about 60°, most preferably about 45°. It should also be noted that the angle between the ports from center-to-center should preferably be not greater than about 90°, more preferably about 30° to about 60°, and most preferably about 45° to achieve a sufficient separation between the ports to minimize interaction between the ports.

Referring to FIG. 7, the operation of the apparatus of this invention will be described. The column of fibers 716 is directed around the flow channel 714 along the splitting member 200 of the splitter chute 32 by the pumping action of the disintegrating element 28. The column of fibers 716 is directed along the curvilinear surface of the splitting member such that angular motion and thus angular velocity and momentum is imparted to each of the fibers in the column. A high velocity column of air is simultaneously directed through the conduit duct 706 and past the port 700. This column of air may be provided by any conventional means (not shown) such as a blower positioned to inject air through the inlet 710 of the conduit duct 706 or a vacuum means positioned downstream of the discharge outlet 712, preferably below the foraminous forming element of the drum-type airlaying apparatus so as to draw ambient air through the inlet 710 of the conduit duct 706.

While not wishing to be bound by theory, by maintaining a column of high velocity air (at least about 6000 feet per minute, and more preferably about 10,000 feet per minute) flowing through the conduit ducts, it is believed that a pressure differential or low pressure zone is created between the pressure in the flow channel and the pressure in the conduit duct adjacent to or below the ports. Because of the pressure differential created by the movement of the column of air and the angular velocity and mass-derived momentum of the fibers, the fibers tend to pull away from the disintegrating element and be directed along the pathway created by the tapered edge of the upstream edge of the port while they are being drawn into the first conduit duct as a result of the pressure differential. Thus the fibers need not be split-off by the mechanical action of a doctor's edge, but are split-off as a result of air and fiber momentum, thereby minimizing clumping due to the absence of mechanical edges or walls.

The stream of fibers which is drawn into the conduit duct subsequently becomes entrained in the column of air, the resultant stream of air-entrained fibers being directed downstream and out of the discharge outlet into the corresponding deposition chute. This process is repeated along each of the ports so as to create multiple, independent streams of air-entrained fibers.

The deposition chutes provide a means for directing streams of air-entrained fibers from the splitter chute 32 to one of the airlaying means and for depositing the fibers onto the airlaying means. The deposition chutes also preferably decelerate the air-entrained fiber streams and orient the fiber streams from the discharge outlets to be compatible with the width and location of the airlaying means.

The deposition chutes may comprise any members that are known in the art that are capable of performing the above functions. Preferably, the deposition chutes comprise ducts that are designed so as to decelerate the fiber streams while minimize clumping of the fibers during their reorientation from the splitter chute to the airlaying means. The deposition chute should be designed to provide a reduction in air speed with a minimum of chute contraction and expansion angles. Preferably, the chutes provide about a two-thirds reduction in air speed and more preferably reduce the air speeds by a factor of 3 so that the fibers do not impact the laydown drum at a high velocity. Thus, the walls of the deposition chutes should have various curves and tapers to provide a gradually increasing cross-sectional area to reduce the velocity of the fiber streams. The deposition chutes preferably have a rectangular cross-sectional area.

As shown in FIG. 7, the first deposition chute 36 preferably comprises a "Y-shaped" configuration so as to merge the first and third fiber streams into a primary or combined fiber stream. Preferably, the first deposition chute 36 is designed to minimize the turbulence encountered with the merging of the two fiber streams. Thus, this chute preferably uses a fifth order polynomial curve profile or other profiles having their first and second derivative equal to zero so as to blend the fiber streams into a single stream.

As shown in FIG. 1, the apparatus 20 and more particularly the first deposition chute 36, is preferably provided with a means for providing discrete particles of absorbent gelling material. The absorbent gelling material injection apparatus 40 or means mixes discrete particles of absorbent gelling material with the combined or primary stream of air-entrained fibers prior to the deposition of the stream onto the first airlaying means. An exemplary type of injection means is shown in U.S. Pat. No. 4,551,191 issued to Ronald W. Kock and John A. Esposito on Nov. 5, 1985, said patent being herein incorporated by reference. The injection means preferably comprises a hopper (not shown) for storing a quantity of absorbent gelling material, a feed device (not shown) for metering the release of absorbent gelling material through an inlet duct 172 into an eductor 174 which entrains the absorbent gelling material in air, and a spreading duct 176 which provides air-entrained absorbent gelling material particles to the fiber streams. The absorbent gelling material is then entrained in and mixed with the fiber streams before the admixture is deposited on the laydown drum. Any other suitable injection means as are known in the art may also be used for the invention. In addition, any of the other deposition chutes may be provided with absorbent gelling material injection means as are required.

The uniting means or apparatus provide a means for uniting the web components. "Uniting" is used herein to denote that the webs are brought together in direct or indirect relationships to form an airlaid fibrous web. While many uniting apparatus are known in the art, a preferred uniting apparatus comprises a pair of uniting rolls upon which a continuous stream of enwrapped insert core components are directed to be positioned adjacent the shaped core components 1008.

Any other uniting means, including embodiments wherein the insert core components are blown-off of the first airlaying means directly onto the shaped core components, are also comtemplated by the present invention.

The first and second airlaying means or apparatus, for forming fibrous webs are shown in FIG. 1 to preferably comprise drum-type airlaying apparatus. While the airlaying apparatus of the present invention may alternatively comprise a number of different configurations such as a moving foraminous screen, a drum-type airlaying apparatus is especially preferred. Typical drum-type airlaying apparatus useful in the present invention are shown in U.S. Pat. No. 4,388,056, issued to F. B. Lee and O. Jobes, Jr., on June 14, 1983, and U.S. patent application Ser. No. 576,098, filed on Feb. 1, 1984 by B. R. Feist, J. E. Carstens and D. A. Peterson, both of which are herein incorporated by reference. While the present invention can be practiced using a drum-type airlaying apparatus either which forms an endless or continuous web or which forms discrete webs or articles, the following description will be related to a drum-type airlaying apparatus for making discrete fibrous webs.

The first drum-type airlaying apparatus 34 is shown in FIG. 1 to comprise a first deposition or laydown drum 100 having a foraminous forming element (not shown) disposed about the drum's periphery; a first scarfing roll 102; a first blow-off means or nozzle 104; a first take-away conveyor 62 disposed about mounting rolls 106; and a first transfer vacuum box 108 positioned beneath the upper run of the take-away conveyor 62. The second drum-type airlaying apparatus 46 preferably comprises a second deposition or laydown drum 110 having a foraminous forming element (not shown); a second scarfing roll 112; a second blow-off means or nozzle 114; a second take-away conveyor 66 disposed about mounting rolls 116; and a second transfer vacuum box 118 positioned beneath the upper run of the second take-away conveyor 66. Means not shown in FIG. 1 include means for driving the drums, differential pressure means including a vacuum plenum duct, fan and a fan drive to draw fiber-depleted air through either the foraminous forming elements and to exhaust the air out of the drum through a duct.

Thus, the apparatus 20 provides a means for converting an endless length or roll of drylap material into a succession of fibrous webs for use as absorbent cores in disposable diapers, catamenial napkins and the like. As shown in FIG. 1, a roll of drylap material 24 is unrolled into a sheet which is advanced to the disintegrator 26. The sheet is fed radially into the disintegrator 26 by the pair of counter-rotating metering infeed rolls 22. An inlet opening 80 in the housing 30 of the disintegrator 26 receives the fibrous sheet and guides it to the inner end of the housing 30 where the edge of the fibrous sheet is disintegrated into a column of fibers disposed across the axial width of the housing 30. The column of fibers is directed around the flow channel 78 by the pumping action of the disintegrating element 28 to the splitter chute 32. The column of fibers is split into multiple fiber streams that are entrained in air by the splitter chute 32, the air-entrained fiber streams being directed out of the splitter chute 32 into the deposition chutes.

A dusting layer fiber stream 56 is directed through the dusting layer deposition chute 42 to the first laydown drum 100 where the fibers are deposited on the foraminous forming element of the first laydown drum 100. Preferably, a first fiber stream 54 and a third fiber stream (not shown) are merged in and directed through the first deposition chute 36 where the combined or primary fiber stream is mixed with discrete particles of absorbent gelling material that are injected into the first deposition chute 36 by the absorbent gelling material injection apparatus 40. The resultant admixture is directed to the first laydown drum 100, whereupon the fiber/absorbent gelling material admixture is deposited and collected on the foraminous forming element over the dusting layer, downstream of the position where the dusting layer was formed. The fiber-depleted entrainment air is drawn through the foraminous forming element by the vacuum maintained behind the foraminous forming element. The resultant first web component is then transferred to the first take-away conveyor 62 by the blow-off nozzle 104 and the transfer vacuum box 108 located under the conveyor belt. The second web component is preferably formed in a similar manner as the first web component by directing a second fiber stream 58 through the second deposition chute 48, by depositing and collecting the second fiber stream 8 on the foraminous forming element of the second laydown drum 100; and by transferring the resultant second web component onto a second take-away conveyor 66.

Before uniting the web components, the web components may be finished by different operations such as calendaring, enwrapping or reinforcing the webs as are known in the art. As shown in FIG. 1, the first web component is enwrapped in tissue by means of a folding board, whereupon the continuous stream of enwrapped first core components is directed to the uniting rolls. The web components are then united by directing the continuous stream of enwrapped first web components over the uniting means or rolls 52 whereupon they are brought into contact with the second web components. Other converting operations as desired may then be effected upon the resultant fibrous web downstream from the uniting means or rolls 52 to produce a finished disposable absorbent article such as a disposable diaper.

Figure 9:
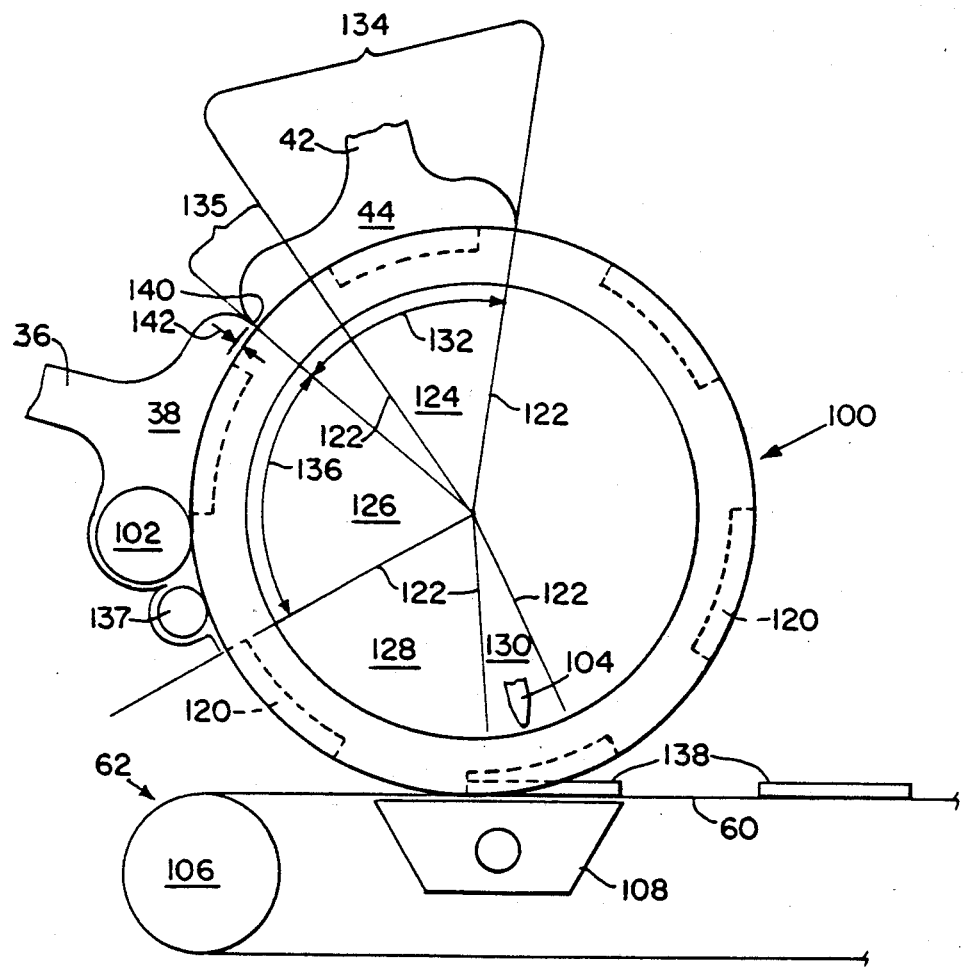
FIG. 9 is an enlarged cross-sectional view of the first airlaying means of the present invention.

FIG. 9 shows an enlarged sectional view of a preferred embodiment of the first drum-type airlaying apparatus 34 of the present invention. As shown in FIG. 9, the apparatus for forming fibrous webs having discrete particles dispersed therein or having a multiplicity of layers preferably comprises a laydown drum 100 having a foraminous forming element consisting of a plurality of formation cavities 120 circumferentially spaced about the periphery of the drum 100. The number of cavities 120 can be varied depending upon the size of the drum 100 or the size of the webs to be formed. In the embodiment shown, the drum 100 contains six cavities. A plurality of ribs 122 are mounted within the interior of the drum 100 to define a dusting layer vacuum chamber 124, a first or primary vacuum chamber 126, a hold-down vacuum chamber 128, and a blow-off chamber 130 having a blow-off means or nozzle 104. Each of the vacuum chambers is connected to a suitable source of vacuum (not shown) by vacuum ducts (not shown). The apparatus also preferably comprises a dusting layer deposition means such as a dusting layer deposition chute 42 and hood 44 for directing a dusting layer stream of air-entrained fibers to a dusting layer sector 132 of the laydown drum 100. The dusting layer hood 38 has a first sector 134 that circumferentially spans the entire dusting layer vacuum chamber 124 and a second sector 135 that circumferentially spans a portion of the first vacuum chamber 126. A first or primary deposition means such as a first deposition chute 36 and hood 38 for directing a first stream of air-entrained fibers to a first sector 136 of the laydown drum 100 is also shown in FIG. 9, the first hood 38 having sufficient circumferential span to enclose the remaining portion of the first vacuum chamber 126. The apparatus further comprises a scarfing roll 102; a sealing roll 137; and a take-away conveyor 62 having an endless stream of discrete fibrous webs 138 or insert core components moving on the conveyor 62.

A critical feature of this invention is that the first vacuum chamber 126 is disposed not only subjacent the entire first hood 38 but also under the downstream or second section 136 of the dusting layer hood 44 so that approximately equal pressures are established adjacent the intersection point 140 of the hoods. Since each of the hoods preferably has a circumferential span of one complete cavity 120 (measured from the edge of a first cavity to the same edge of a second cavity) or approximately 60 degrees for a six cavity drum, the first vacuum chamber 126 must have a circumferential span of greater than one chamber or about 75 degrees for the embodiment shown in FIG. 9. Although the circumferential span of that portion of the first vacuum chamber 126 under the dusting layer hood 44 (i.e. the circumferential span of the second sector 136 of the dusting layer hood 44) has not been found to be particularly critical, there should be sufficient circumferential span as to allow a minimal transition zone between the dusting layer hood 44 and the first hood 38. This minimal circumferential span decreases as the number of cavities 120 increases and increases as the number of cavities 100 decreases.

Another critical feature is that a small gap 142 must exist between the outer surface of the laydown drum 100 and the point of intersection 140 of the hoods to allow for equalization of pressure in the portions of each hood adjacent the intersection point. If no gap existed, then there could be differential pressures in each hood so that as the drum brought the edge of the dusting layer into the first hood 38, this pressure differential could cause the dusting layer to lift off of the screen or shear. If the gap is too large, the two deposition chutes essentially merge into one and the independent dusting layer concept is not achieved. Thus a gap 142 of not more than about one-half inch is desirable with a one-eighth inch gap being preferable so that the pressure may equalize in each portion of each hood that is adjacent to the intersection point 140.

Another important design criteria is that each of the hoods should have a relatively wide circular taper near the intersection point 140 so that the fibers that are directed toward the laydown drum in this area do not impinge on the dusting layer at an acute angle. When fibers impinge upon the dusting layer at an acute angle, the fibers have a component of velocity which is parallel to the surface of the drum, thus the fibers tend to cause the fibers constituting the dusting layer to lift or shear. The critical shear velocity has been determined to be about 4000 feet per minute; the chute geometry being designed with this as a limiting factor. Thus it is desirable that the fibers impinge upon the fibers of the dusting layer at an angle as close to perpendicular as possible because the shear component would not exist. Thus, each of the hoods should have a relatively wide circular taper so that the fibers do not impinge upon the dusting layer at an acute angle or exceed the critical shear velocity. As shown in FIG. 9, each of the hoods has about a three inch radius of curvature adjacent the intersection point.

The operation of the apparatus is as follows. The dusting layer stream of fibers is directed toward a circumferential span or dusting layer section 132 of the periphery of the laydown drum 100 through the dusting layer deposition chute 42 and the dusting layer hood 44. The circumferential span preferably being equal to the span of one cavity 120 or about 60° degrees if six cavities 120 are used. The fibers are deposited onto the foraminous forming element of one of the cavities 120 on the drum 100 while the entrainment air is being drawn through the foraminous forming element by the vacuum maintained in the dusting layer vacuum chamber 124 as well as by the vacuum maintained in the primary or first vacuum chamber 126. Thus the dusting layer is formed by the collected fibers on the foraminous forming element.

As the drum rotates, the dusting layer passes from the influence of the dusting hood 44 to the influence of the first hood 38 where a first stream of air-entrained fibers are being directed generally radially toward the periphery of the drum. However, it should be noted that the dusting layer has already been transferred to the influence of the first vacuum chamber 126 prior to passing between the hoods such that the pressure differential and velocity of the first stream do not have a tendency to shear the dusting layer apart. The fibers of the first fiber stream are thus deposited over the dusting layer while the entrainment air is drawn through the foraminous forming element by the vacuum maintained in the primary or first vacuum chamber 126. The first or primary layer is formed by the collected fiber/AGM admixture over the dusting layer. Since the dusting layer is substantially left intact, discrete particles of absorbent gelling material do not tend to be drawn through the foraminous forming element nor plug it due to the block effect of having a layer of fibers already covering the void spaces in the foraminous forming element.

The resultant fibrous web then passes under the scarfing roll 102 where the web is leveled. The fibrous web 138 or insert core component is then transferred to the take-away conveyor 62 by the joint action of the blow-off nozzle 104 and the vacuum maintained underneath the conveyor belt. The fibrous web 138 is then conveyed downstream to subsequent converting operations to produce a finished disposable absorbent articles such as a disposable diaper.

While particular embodiments of the present invention have been illustrated and described, it would be obvious to those skilled in the art that various changes and modifications can be made without departing from the spirit and scope of the invention. It is intended to cover, in the appended claims, all such modifications and intended uses.

What is claimed is:

1. An absorbent article comprising:
   a topsheet;
   a liquid impervious backsheet associated with said topsheet; and
   a dual-layer absorbent core disposed between said topsheet and said backsheet, said dual-layer absorbent core comprising:
   (i) a shaped core component that quickly collects and distributes discharged body liquids, and
   (ii) an insert core component that absorbs and retains discharged body fluids from said shaped core component, said shaped core component being positioned between said topsheet and said insert core component, said insert core component comprising:
   (a) a dusting layer consisting of hydrophilic fiber material, and
   (b) a primary layer consisting of a combination of hydrophilic fiber material and particular amounts of discrete particles of absorbent gelling material airlaid over said dusting layer,
   wherein said dusting layer is relatively thinner in thickness than said primary layer, and wherein said dusting layer is disposed adjacent said backsheet.

2. The absorbent article of claim 1 wherein said primary layer comprises a uniform combination of hydrophilic fiber material and particular amounts of discrete particles of absorbent gelling material.

3. The absorbent article of claim 2 wherein said hydrophilic fiber material consists of cellulose fibers.

4. The absorbent article of claim 3 wherein said insert core component has a top surface area from about 0.25 to about 1.0 times that of said shaped core component.

5. The absorbent article of claim 4 wherein said insert core component is positioned relative to said backsheet in a manner such that at least about 75% of the absorbent gelling material in said primary layer is found within the front two-thirds section of said absorbent article.

6. The absorbent article of claim 5, wherein said primary layer contains from about 9% to about 60% by weight of said primary layer of discrete particles of absorbent gelling material.

7. The dual-layer absorbent core of claim 6 wherein said shaped core component consists essentially of hydrophilic fiber material and from about 0% to about 8% by weight of said shaped core component of discrete particles of absorbent gelling material.

8. An absorbent article comprising:
a topsheet;
a liquid impervious backsheet associated with said topsheet; and
an absorbent core disposed between said topsheet and said backsheet, said absorbent core comprising:
(a) a dusting layer consisting of hydrophilic fibrous material, and
(b) a primary layer consisting of a combination of hydrophilic fibrous material and particular amounts of discrete particles of absorbent gelling material airlaid over said dusting layer,
wherein said dusting layer is relatively thinner in thickness than said primary layer, and wherein said dusting layer is positioned adjacent said backsheet.

9. The absorbent article of claim 8 wherein said primary layer consists of a uniform combination of hydrophilic fibrous material and particular amounts of discrete particles of absorbent gelling material.

10. The absorbent article of claim 9 wherein said hydrophillic fibrous material comprises cellulose fibers.

* * * * *

UNITED STATES PATENT AND TRADEMARK OFFICE
CERTIFICATE OF CORRECTION

PATENT NO. : 4,888,231
DATED : December 19, 1989
INVENTOR(S) : JOHN J. ANGSTADT

It is certified that error appears in the above-identified patent and that said Letters Patent is hereby corrected as shown below:

| | |
|---|---|
| Column 1, Line 39, | "Dawn 1. Houghton" should read ---Dawn I. Houghton---. |
| Column 3, Line 31, | "Dawn 1. Houghton" should read ---Dawn I. Houghton---. |
| Column 3, Line 34, | "hold and distribute discharge" should read ---hold and distribute discharged---. |
| Column 3, Line 50, | "1008 absorbs discharge" should read ---1008 absorbs discharged---. |
| Column 5, Line 4, | "the term "disintegrator" s" should read ---the term "disintegrator" is---. |
| Column 6, Line 63, | "However, alternative preferred slitting" should read ---However, alternative preferred splitting---. |
| Column 9, Line 15, | "Thus it is preferably" should read ---Thus it is preferable---. |
| Column 9, Line 58, | "it is preferably" should read ---it is preferable--. |
| Column 12, Line 14-15, | rotating in a comput-er-clockwise direction" should read ---rotating in a computer-clockwise direction--. |
| Column 12, Line 20, | "plate 708, the inlet" should read ---plate 708; the inlet---. |
| Column 16, Line 1, | "stream 8" should read ---stream 58---. |

UNITED STATES PATENT AND TRADEMARK OFFICE
CERTIFICATE OF CORRECTION

PATENT NO. : 4,888,231

DATED : December 19, 1989

INVENTOR(S) : John J. Angstadt

It is certified that error appears in the above-identified patent and that said Letters Patent is hereby corrected as shown below:

Column 18, Line 26,     "disposable absorbent articles" should read ----disposable absorbent article---.

Signed and Sealed this

Sixteenth Day of June, 1992

Attest:

DOUGLAS B. COMER

*Attesting Officer*      *Acting Commissioner of Patents and Trademarks*